US008221307B2

(12) United States Patent
Duchene

(10) Patent No.: US 8,221,307 B2
(45) Date of Patent: Jul. 17, 2012

(54) ELECTRONIC ENDOSCOPE

(75) Inventor: Arnaud Duchene, Longjumeau (FR)

(73) Assignee: Optomed, Courtaboeuf (FR)

( * ) Notice: Subject to any disclaimer, the term of this patent is extended or adjusted under 35 U.S.C. 154(b) by 534 days.

(21) Appl. No.: 12/402,715

(22) Filed: Mar. 12, 2009

(65) Prior Publication Data

US 2009/0234185 A1 Sep. 17, 2009

(30) Foreign Application Priority Data

Mar. 13, 2008 (FR) ...................................... 08 51639

(51) Int. Cl.
*A61B 1/04* (2006.01)
*A61B 1/00* (2006.01)
(52) U.S. Cl. ....................................... 600/110; 600/102
(58) Field of Classification Search .................. 600/143, 600/144, 146, 150
See application file for complete search history.

(56) References Cited

U.S. PATENT DOCUMENTS

| | | | |
|---|---|---|---|
| 4,633,304 A | | 12/1986 | Nagasaki |
| 5,345,937 A | * | 9/1994 | Middleman et al. .......... 600/434 |
| 7,104,951 B2 | * | 9/2006 | Hasegawa et al. ............ 600/102 |
| 7,303,560 B2 | * | 12/2007 | Chin et al. ....................... 606/41 |
| 2002/0068851 A1 | * | 6/2002 | Gravenstein et al. ......... 600/121 |
| 2002/0156391 A1 | * | 10/2002 | Derksen et al. ............... 600/529 |
| 2007/0249899 A1 | * | 10/2007 | Seifert .......................... 600/109 |
| 2010/0063437 A1 | * | 3/2010 | Nelson et al. ................... 604/35 |
| 2011/0092768 A1 | * | 4/2011 | Emanuel et al. .............. 600/109 |
| 2011/0130628 A1 | * | 6/2011 | Smith et al. ................... 600/114 |

FOREIGN PATENT DOCUMENTS

| | | |
|---|---|---|
| WO | 0128407 | 4/2001 |
| WO | 2008004111 A2 | 1/2008 |

OTHER PUBLICATIONS

Priority Search Report dated Oct. 6, 2008, in French priority.

* cited by examiner

*Primary Examiner* — Philip R Smith
*Assistant Examiner* — William Chou
(74) *Attorney, Agent, or Firm* — Young & Thompson

(57) ABSTRACT

An electronic endoscope (2) of the type including: a distal end (14) including an illumination element and an electronic image acquisition member; a probe (12), one of the ends of which is connected to the distal end; and control elements (10) connected to the other end of the probe, characterized in that the probe includes a plastically malleable portion (20) suitable for preserving, under the effect of its own weight when the endoscope is in use, the shape which has been conferred on it by an operator, the malleable portion carrying the distal end of the endoscope.

11 Claims, 3 Drawing Sheets

ELECTRONIC ENDOSCOPE

The present invention relates to an electronic endoscope of the type comprising: a distal end comprising an illumination means and an electronic image acquisition means; a probe, one of the ends of which is connected to the distal end; and control means connected to the other end of the probe.

BACKGROUND OF THE INVENTION

Some respiratory pathologies of the larynx or pharynx of a member of the Equidae, and in particular of a racehorse, can be diagnosed only by an endoscopic examination carried out in the course of a dynamic test, using an endoscope, preferably an electronic endoscope.

According to the prior art, the control means of an electronic endoscope comprises a light source producing a luminous flux which is guided along the probe as far as the distal end by means of an optical fibre. The illumination means of the distal end comprises lenses enabling the luminous flux received from the optical fibre to be distributed on the zone to be examined. The light source of the known electronic endoscopes has a large space requirement and requires a high-power electric current generator, which also has a large space requirement. Consequently, the electronic endoscopes according to the prior art are fixed instruments.

This is why the dynamic test is carried out on dedicated premises equipped with an endoscopy installation comprising a fixed electronic endoscope and a specific treadmill on which the racehorse to be examined is placed.

Use is made of a pliable electronic endoscope, the probe of which is soft and non-self-supporting. This mechanical characteristic of the probe is used to position the distal end. More precisely, the distal end is introduced via the nostrils and then pushed into the animal's sinuses, in order to be placed in the animal's throat, facing the zone to be examined. The probe which carries the distal end then abuts the walls of the sinuses and of the cavity to be inspected.

However, in this test environment, the animal is not really under normal training conditions. The trauma of being placed on a treadmill distorts the animal's behaviour, which reduces the value of such an examination accordingly.

In addition, an endoscopy installation comprising a treadmill is extremely expensive. Furthermore, since this installation is fixed, it is necessary to transport the racehorse to the examination premises, which represents an additional cost when these premises are at a long distance from the training centre.

Finally, the image obtained is not of high quality because the distal end carried by the soft probe and comprising the electronic image acquisition means is displaced relative to the zone to be examined in the course of the dynamic test and the animal's movements. In extreme cases, such as a sudden movement of the animal's head, the distal portion may come into contact with the mucous membranes.

SUMMARY OF THE INVENTION

The object of the invention is therefore to provide a solution to the above-mentioned problems by proposing an electronic endoscope enabling an endoscopy to be carried out under normal conditions, for example racehorse training conditions, while ensuring a good image quality.

To that end, the invention relates to an electronic endoscope of the above-mentioned type, characterized in that the probe comprises a plastically malleable portion capable of preserving, under the effect of its own weight when the endoscope is in use, the shape which has been given to it by an operator, the malleable portion carrying the distal end of the endoscope.

According to particular embodiments of the invention, the electronic endoscope comprises one or more of the following features, taken in isolation or in accordance with any technically possible combination:

- the illumination means comprises at least one LED.
- the control means comprises a battery as a means of generating electric current suitable for supplying the endoscope with electrical power, the endoscope thus being rendered autonomous.
- the malleable portion comprises at least one rod which is produced from a suitable malleable material and a cross-section of which has suitable dimensions, so that the rod confers the desired plasticity on the malleable portion.
- the malleable portion comprises two rods produced from a material which conducts the electric current, and the two rods enable the battery to be connected electrically to the illumination means of the distal end.
- the control means comprises a means for emitting and transmitting radio waves in order to communicate with a corresponding means for emitting and transmitting radio waves which is arranged at a distance.
- the control means comprises a processing means enabling the signals generated by the electronic image acquisition means to be processed in real time in order to produce images, it being possible for the images produced to be displayed in real time on a display means connected to the corresponding means for emitting and transmitting radio waves which is arranged at a distance.
- the endoscope is suitable for carrying out an endoscopic examination on a racehorse in the course of a normal training session thereof.
- the rod is produced from a copper alloy, preferably comprising 90% by weight of copper, and has a diameter of from 1.7 to 2.5 mm, and preferably from 1.75 to 2.25 mm.
- the endoscope comprises a halter provided with a means for securing the probe, the securing means preferably comprising at least one clip enabling the probe to be secured by clipping.

BRIEF DESCRIPTION OF THE DRAWINGS

The invention and its advantages will be better understood on reading the following description which is given purely by way of example and with reference to the appended drawings, in which.

DETAILED DESCRIPTION OF THE PREFERRED EMBODIMENTS

Figure 1:
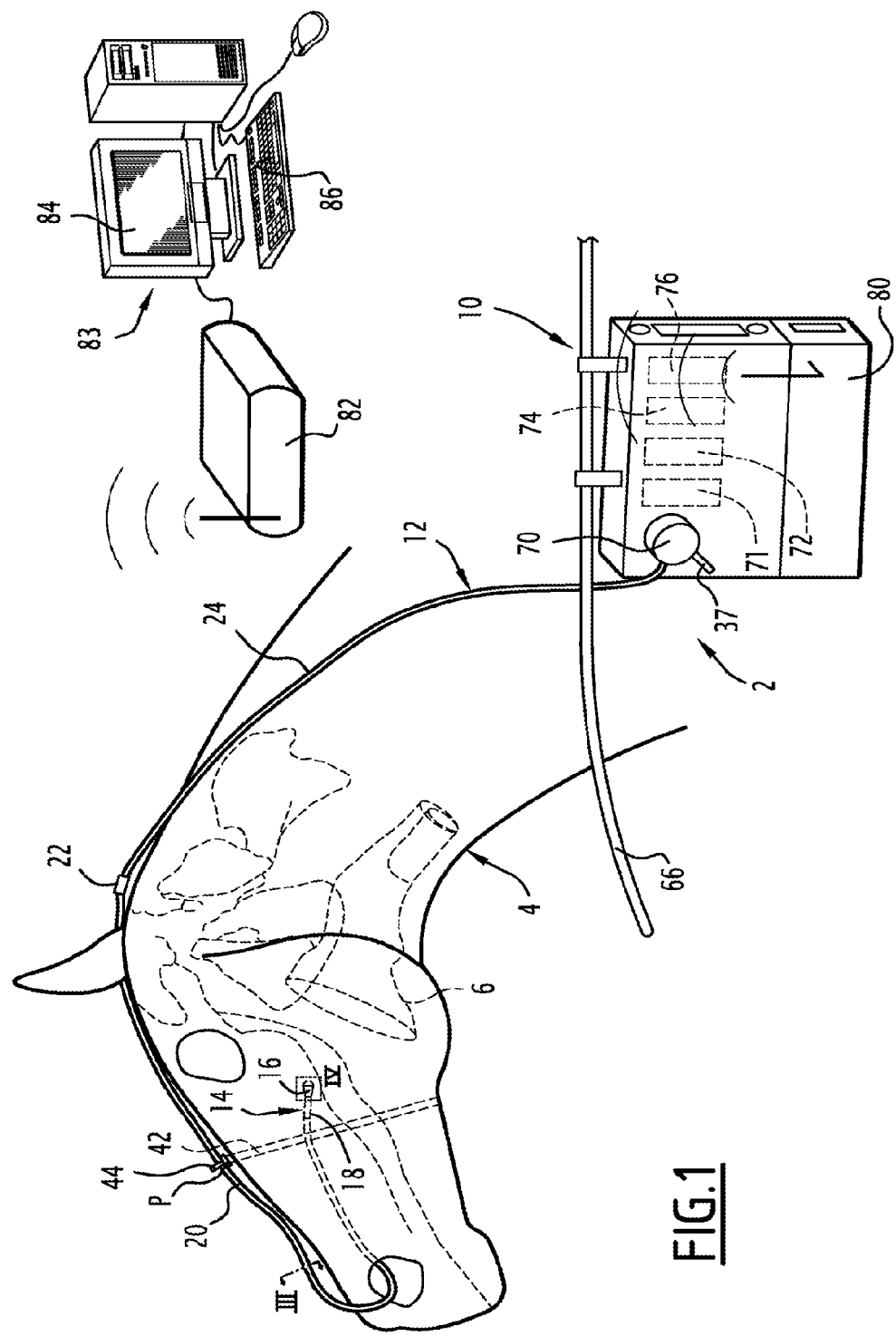
FIG. 1 is a diagrammatic representation of the electronic endoscope according to the invention in the examining position on a racehorse.

FIG. 1 illustrates diagrammatically the electronic endoscope 2 according to the invention. The electronic endoscope 2 is shown in position on the head of a horse 4. It is desired to examine the larynx 6 of horse 4 in the course of a dynamic test carried out under the normal conditions of a training session.

The electronic endoscope 2 comprises control means 10, a probe 12, and a distal end 14. The distal end 14 is connected mechanically and electrically to the control means 10 by way of the probe 12.

The distal end 14 comprises a head 16 and an articulated portion 18. The head 16 comprises a means for illuminating the cavity to be examined, and also an electronic image acquisition means suitable for generating an electrical video signal. As will be described in detail in the description of the head 16 with reference to FIG. 4, the illumination means comprises several electroluminescent diodes, or LEDs, and the electronic image acquisition means comprises a charge transfer sensor, or CCD sensor.

The articulated portion 18, secured to the rear of the head 16, connects the head 16 to one of the ends of the probe 12. The articulated portion 18 comprises first and second displacement means enabling the head 16 to be oriented mechanically in two mutually perpendicular directions.

The control means 10 will now be described in detail.

Since the illumination means of the electronic endoscope 2 according to the invention is constituted by LEDs, the control means 10 do not comprise a light source, unlike the prior art. Furthermore, the LEDs consume a small amount of electrical power, so that the control means 10 of the endoscope 2 comprise a generator of electric current which is a battery 72 having small dimensions. Consequently, the control means 10 are compact and transportable. They are carried by the subject to be examined. In the case of a racehorse, the control means 10 can be placed in the saddle, in a rucksack carried by the rider or, as shown in FIG. 1, secured to an arm 66 of the sulky drawn by the horse 4. The electronic endoscope according to the invention weighs less than 5 kg.

The control means 10 comprise a casing 70 for the mechanical and electrical connection of the probe 12; first and second drive means 71 for operating the first and second displacement means, respectively, of the articulated portion 18; the battery 72 for the supply of electric current to the endoscope 2; a processor 74 suitable, inter alia, for processing the video signal transmitted from the electronic image acquisition means; and a storage means 76 enabling the images decoded by the processor 74 to be recorded in real time.

The control means 10 also comprise a means 80 for emitting and receiving radio signals. The emitting and receiving means 80 is to communicate with a corresponding emitting and transmitting means 82 based on the ground and at a remote distance. The corresponding emitting and transmitting means 82 is, for example, connected to a computer 83 having a screen 84, and a keyboard 86, and constituting a control and monitoring interface for the operator. In particular, the operator watches in real time, on the screen 84, the image acquired by the electronic endoscope 2, throughout the installation of the endoscope 2 and in the course of the dynamic test.

The first and second drive means for operating the first and second displacement means, respectively, of the articulated portion 18 may assume the form of first and second thumb wheels on the control casing 70. These first and second thumb wheels are used by the operator to orient the head 16 of the endoscope in a suitable manner during an initial stage of installing the endoscope, before carrying out the dynamic test. Preferably, the first and second drive means are actuators 71 suitable for being remote-controlled by the operator by means of the computer 83 and the radio communication means 80 and 82.

The probe 12 is connected, at one of its ends, to the articulated portion 18 of the distal end 14 and is coupled, at the other end, to the connecting casing 70 of the control means 10. The function of the probe 12 is to connect the control means 10 electrically to the illumination means and to the image acquisition means of the head 16, and to connect the control means 10 mechanically to the articulated portion 18.

Furthermore, the function of the probe 12 of the electronic endoscope 2 according to the invention is to hold the distal end 14 in a predefined position inside the cavity to be examined. For that purpose, the probe 12 comprises, in succession along its length, a malleable portion 20, a connecting element 22 and a passive portion 24. The malleable portion 20 extends between the articulated portion 18 of the distal end 14 and the connecting means 22. The passive portion 24 extends between the connector 22 and the connecting casing 70.

Figure 3:
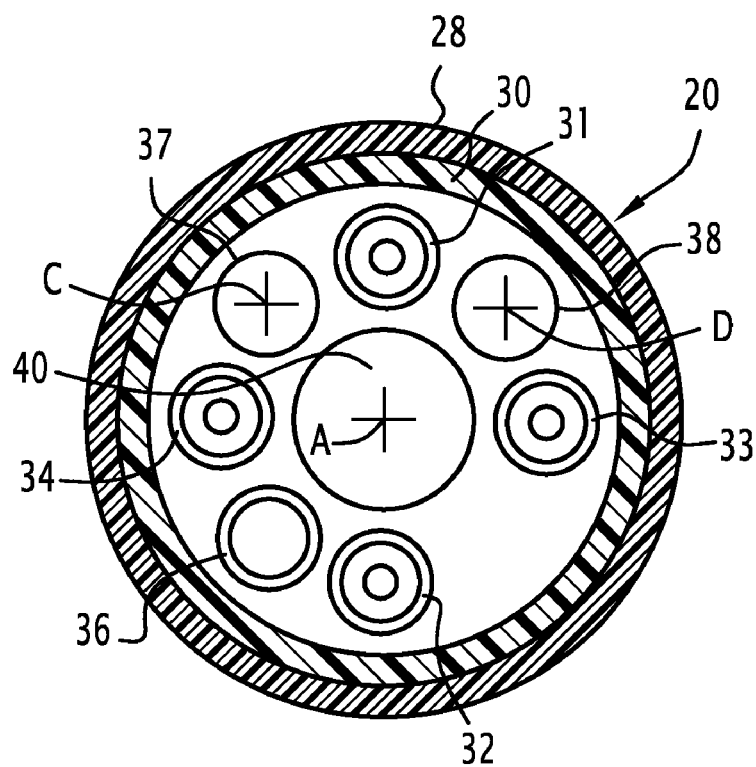
FIG. 3 is a cross-section through the malleable portion of the endoscope of FIG. 1.

The malleable portion 20 of the probe 12 will now be described in detail with reference to FIG. 3 which shows a cross-section thereof. The malleable portion 20 is locally of a cylindrical shape about an axis A. It has a diameter of less than 1 cm. It is delimited externally by a tubular sleeve 28 composed of a plastics material, such as, for example, PVC. The face oriented radially towards the inside of the sleeve 28 is reinforced by a helical metal strip 30. The latter constitutes a reinforcement of the malleable portion 20 permitting deformation by bending in an axial plane.

Inside the volume delimited by the helical metal strip 30, the malleable portion 20 of the probe 12 comprises a first pair of cables 31 and 32 which are to be coupled, on the one hand, to the first mechanical displacement means of the articulated portion 18 and, on the other hand, to the first drive means of the control means 10 in order to orient the head 16 in the first direction. The malleable portion 20 also comprises a second pair of cables 33 and 34 which are to be coupled, on the one hand, to the second mechanical means of the articulated portion 18 and, on the other hand, to the second drive means of the control means 10 in order to orient the head 16 in the second direction.

The probe 12 also comprises an irrigation duct 36 enabling air and/or water to be brought from an inlet orifice 37 located on the connecting casing 70 to an outlet orifice 35 located on the head 16 of the distal end 14. The irrigation duct 36 therefore extends through the passive portion 24, the connector 22, the malleable portion 20, the articulated portion 18 and the head 16.

The malleable portion 20 of the probe 12 comprises at least one resiliently malleable rod. In the embodiment described, the malleable portion 20 comprises a first rod 37 and a second rod 38. The first and second rods 37 and 38 are cylindrical and their respective axes C and D are arranged parallel with the axis A. The function of the first and second rods 37 and 38 is to confer on the malleable portion 20 the mechanical characteristic of being both plastically malleable and rigid: to be more precise, the malleable portion 20 is plastically malleable because it is capable of being deformed during the application of reasonable stresses, that is to say, stresses which can be generated by the muscular force of an operator, and then of keeping the shape thus given by the operator while the deformation stress has ceased to be applied; the malleable portion 20 is rigid in the sense that it keeps the shape given by the operator in the course of the use of the endoscope, that is to say, the malleable portion 20 has a sufficient rigidity with respect to the stresses generated during the dynamic test, by the weight and the accelerations of the malleable portion 20.

Preferably, the first rod 37 and/or the second rod 38 is/are produced from a malleable material.

The function of the first and second rods 37 and 38 is also to conduct the electric current from the battery 72 to the illumination means of the head 16. Preferably, the first rod 37 and/or the second rod 38 is/are then produced from a material which conducts the electric current.

In the currently preferred embodiment, the first and second rods 37 and 38 are composed of a metal material, preferably a copper alloy.

For an electronic endoscope according to the invention suitable for carrying out an endoscopic examination on a racehorse, the malleable portion 20 is placed on the animal's head in such a manner that it projects, beyond a securing point P, over a length of approximately 1 meter. The first and second rods 37 and 38 are produced from an alloy of 90% by weight of copper and have a diameter of from 1.5 to 2.5 mm, and preferably from 1.75 to 2.25 mm. The first and second rods 37 and 38 do not have to have the same diameter.

It will be appreciated that, in the passive portion 24 of the probe 12, which portion is flexible without preserving its shape, first and second conventional electrical wires are substituted for the first and second rods 37 and 38 of the malleable portion 20. The first and second electrical wires are connected electrically, on the one hand, to the first and second rods 37 and 38 and, on the other hand, to the battery 72, via the connecting casing 70.

Finally, the malleable portion 20 comprises a video cable 40 arranged, for example, along the axis A. The video cable 40 is to transmit the video signal generated by the electronic image acquisition means of the head 16 to the processing means 74 of the control means 10. The video cable 40 therefore extends from the electronic image acquisition means to the connecting casing 70.

Figure 2:
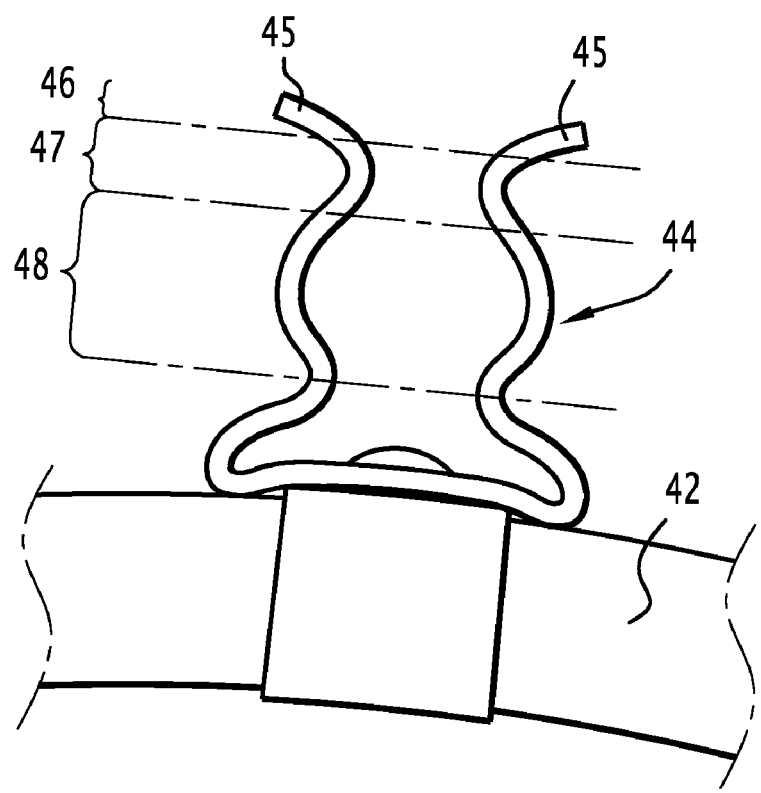
FIG. 2 is a front view of the clip of the means for securing the endoscope of FIG. 1.

The electronic endoscope 2 comprises means for securing it to the subject to be examined. In the case of a racehorse, the probe 12 is secured to a specific halter 42 comprising a clip 44 shown in detail in FIG. 2. The steel clip 44 is riveted on to the leather halter 42. The clip 44 is configured in such a manner that the probe 12 is secured by clipping. To be more precise, the clip 44 comprises two lateral arms 45. In an upper section of the clip 44, the two lateral arms 45 spread apart from each other in such a manner as to provide the clip 44 with a guide section 46 in the shape of a "V" which is to help to guide the probe 12 when it is being secured. Then, in an intermediate section, the two arms 45 are close to each other in order to form a necked section 47, the width of which is smaller than the diameter of the probe 12. Finally, in a lower section, the two arms 45 are configured in the shape of arcs of a circle, the diameter of which corresponds to that of the probe 12, in order to define a section 48 for holding the probe in position. The probe is brought into abutment with the two lateral arms 45 in the region of the necked section 47. The operator inserts the probe 12 by force between the two lateral arms 45 which move apart resiliently from each other until the probe 12 can pass through the necked section 47 and be accommodated in the holding section 48. Once in position in the holding section 48, the probe 12 can rotate about its axis A in such a manner that the operator can, for example, align the first direction of displacement of the head 16 of the endoscope 2 in the vertical direction.

Figure 4:
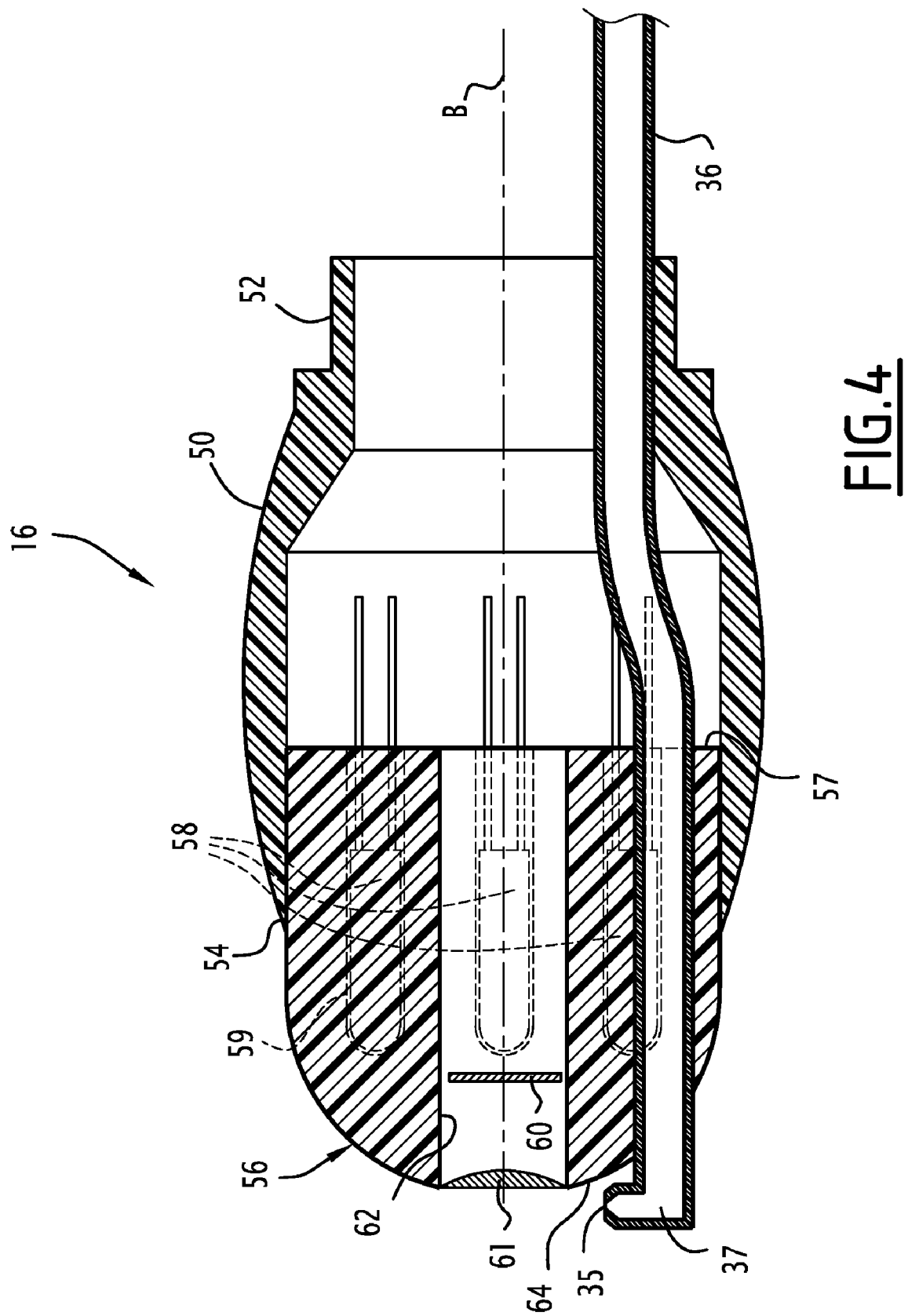
FIG. 4 is an axial section through the head of the distal end of the endoscope of FIG. 1.

Referring now to FIG. 4, the head 16 of the electronic endoscope 2 will be described in detail. It will be observed that such an endoscope head can be reused irrespective of the above-mentioned characteristics of the endoscope. The head 16 comprises a housing 50 having a cylindrical shape about an axis B. The rear edge 52 of the housing 50 comprises a shoulder which is abutted by the tubular articulated portion 18. The front edge 54 of the housing 50 carries a translucent wall 56 closing the front of the housing 50. The wall is composed, for example, of plexiglass. The translucent wall 56 is curved in such a manner as to form a hemispherical cap projecting axially beyond the front edge 54 of the housing 50.

In the interior volume of the housing 50, the head 16 comprises an illumination means constituted by at least one LED 58 and preferably by six LEDs 58. The LEDs 58 are supplied with electric current by the battery 72, via the connecting casing 70, the first and second electrical wires of the passive portion 24, the connector 22, the first and second rods 37 and 38 of the malleable portion 20 of the probe 12 and electrical connectors in the region of the articulated portion 18. The LEDs 58 are selected to produce a luminous flux characterized by a temperature of 6000°, which corresponds to natural light, so that the images obtained by means of the endoscope 2 are of high quality. In the embodiment described, six LEDs 58 are arranged regularly along a ring having an axis B. Thus, the intensity of the luminous flux produced by the head 16 is very uniform in the conical illumination field. A LED 58 of oblong shape is arranged parallel with the axis B in a bore 59 provided in the internal face 57 of the translucent wall 56. Thus, a LED 58 is placed in front of the front edge 54 of the opaque housing 50. The conical illumination field therefore has a wide opening of the order of 140°. The wall 56 is selected to be translucent in order to diffuse the light generated by the various LEDs 58 and to improve the uniformity of the illumination produced. Since the efficiency of the illumination means used in the head 16 of the endoscope 2 according to the invention is very high, it will be appreciated that there is no longer any need to use lenses to concentrate the luminous flux generated.

The head 16 also contains an electronic image acquisition means. This involves a CCD sensor 60, an objective lens 61 and the low-level acquisition electronics required to generate a video signal. The video signal generated is transmitted to the processor 74 via a suitable connector in the articulated portion 18, the video cable 40 extending along the probe 12 and the connecting casing 70. The CCD sensor 60 is accommodated in an axial recess 62 extending through the translucent wall 56. The axial recess 62 is closed in the region of the external face 64 of the translucent wall 56 by the objective lens 61 which has a flat external diopter. The CCD sensor 60 is located along the axis B, behind the objective lens 61, but in front of the LEDs 58. Optionally, the axial wall of the recess 62 is opacified so that the CCD sensor is not disturbed by the light produced by the LEDs 58.

The irrigation duct 36 of the probe 12 continues into the distal end 14 and extends through the translucent wall 56. It terminates in a nozzle 37 placed on the external face 64 of the translucent wall 56. An internal duct of the nozzle 37 forms an elbow at 90° relative to the axis of the irrigation duct 36 and is oriented in such a manner as to project air and/or water onto the objective lens 61 of the electronic image acquisition means via an orifice 35.

The electronic endoscope according to the invention therefore enables an endoscopic image to be produced while the subject is under normal conditions.

Once positioned, the electronic endoscope according to the invention enables a good-quality image to be obtained thanks to the illumination means which generates a high and uniform luminous power, an articulated portion enabling the image acquisition means to be displaced in such a manner as to centre the zone to be examined.

The distal end of the electronic endoscope is suspended inside the cavity to be imaged but does not oscillate in the course of the dynamic test. It follows the movements of the horse's head and there is no risk that it will come into contact with the mucous membranes of the cavity under inspection. The malleable portion can be configured by the operator in such a manner as to follow the anatomical curvature of the ducts moved through to gain access to the cavity to be inspected.

The person skilled in the art will appreciate that, since the electronic endoscope according to the invention is free from optical fibres, it can be deformed in such a manner as to adopt any curvature without this having any influence on the quality of the image obtained.

The invention claimed is:

1. An electronic endoscope of the type comprising:
   a distal end comprising an illumination means and an electronic image acquisition means;
   a probe having a first end and an opposite second end, the first end connected to the distal end; and
   control means connected to the second end of the probe, the control means comprising a battery as a generator of electric current for the supply of electric current to the endoscope, the probe connecting electrically the control means to the illumination means and the electronic image acquisition means, the control means being free of a light source,
   wherein the probe comprises a plastically malleable portion configured to preserve, under the effect of a weight of the probe when the endoscope is in use, a shape provided by an operator, said malleable portion carrying the distal end of the endoscope,
   wherein the malleable portion comprises at least one rod which is produced from a malleable material, said material and the cross-section of said at least one rod being suitable so that said at least one rod confers the desired plasticity on the malleable portion, and
   wherein said at least one rod comprises a material that conducts the electrical current, said at least one rod connecting electrically the battery to the illumination means.

2. The endoscope according to claim 1, wherein the malleable portion comprises a first and a second of said at least one rod, said first and second rods electrically connecting the battery to the illumination means of the distal end.

3. The endoscope according to claim 1, wherein the illumination means comprises at least one LED.

4. The endoscope according to claim 1, wherein the control means comprises a means for emitting and transmitting radio waves in order to communicate with a corresponding means for emitting and transmitting radio waves which is arranged at a distance from the control means.

5. The endoscope according to claim 4, wherein the control means comprises a processing means configured to process the signals generated by the electronic image acquisition means in real time in order to produce images for display in real time on a display means connected to the corresponding means for emitting and transmitting radio waves.

6. The endoscope according to claim 1, wherein the probe and the distal end are structured for carrying out an endoscopic examination on a racehorse in the course of a normal training session thereof.

7. The endoscope according to claim 6, further comprising: a halter provided with a means for securing the probe.

8. The endoscope according to claim 7, wherein the securing means comprises at least one clip configured to secure the probe to the halter.

9. The endoscope according to claim 1, wherein said at least one rod is produced from a copper alloy, and has a diameter of from 1.7 to 2.5 mm.

10. The endoscope according to claim 9, wherein said at least one rod comprises 90% by weight of copper.

11. The endoscope according to claim 9, wherein said at least one rod has a diameter of from 1.75 to 2.25 mm.

* * * * *